US009688023B2

(12) United States Patent
Dean et al.

(10) Patent No.: US 9,688,023 B2
(45) Date of Patent: Jun. 27, 2017

(54) CONTINUOUS DIGITAL LIGHT PROCESSING ADDITIVE MANUFACTURING OF IMPLANTS

(76) Inventors: H. David Dean, Shaker Heights, OH (US); Jonathan E. Wallace, Chardon, OH (US); Antonios G. Mikos, Houston, TX (US); Martha Wang, Fulton, MD (US); Ali Siblani, Dearborn Heights, MI (US); Kyobum Kim, Pittsburgh, PA (US); John P. Fisher, Kensington, MD (US)

( * ) Notice: Subject to any disclaimer, the term of this patent is extended or adjusted under 35 U.S.C. 154(b) by 845 days.

(21) Appl. No.: 13/817,612

(22) PCT Filed: Aug. 22, 2011

(86) PCT No.: PCT/US2011/048620
§ 371 (c)(1),
(2), (4) Date: Jul. 26, 2013

(87) PCT Pub. No.: WO2012/024675
PCT Pub. Date: Feb. 23, 2012

(65) Prior Publication Data
US 2013/0304233 A1    Nov. 14, 2013

Related U.S. Application Data

(60) Provisional application No. 61/375,353, filed on Aug. 20, 2010, provisional application No. 61/491,194, filed on May 29, 2011.

(51) Int. Cl.
*B29C 67/00* (2017.01)
*A61L 27/50* (2006.01)
(Continued)

(52) U.S. Cl.
CPC .......... *B29C 67/0066* (2013.01); *A61L 27/50* (2013.01); *A61L 27/56* (2013.01); *A61L 27/60* (2013.01); *G02B 26/0833* (2013.01)

(58) Field of Classification Search
CPC ............ B29C 67/0062; B29C 67/0066; B29C 67/007
(Continued)

(56) References Cited

U.S. PATENT DOCUMENTS 4,436,684 A    3/1984  White
4,976,737 A    12/1990 Leake
(Continued)

FOREIGN PATENT DOCUMENTS

GB    2 324 470        10/1998
WO    2012/024675 A1   2/2012

OTHER PUBLICATIONS

International Search report issued in corresponding International Application No. PCT/US2011/048620 on Apr. 3, 3014.
(Continued)

*Primary Examiner* — Timothy Kennedy
(74) *Attorney, Agent, or Firm* — Renner, Otto, Boisselle & Sklar, LLP.

(57) ABSTRACT

A process for additive manufacturing of a resorbable implant to be implanted into a patient includes providing a biocompatible resin including a liquid light-polymerizable material that is resorbable after polymerization and an initiator. The process further includes actuating an additive manufacturing apparatus to expose an amount of the biocompatible resin to light to at least partially cure the exposed amount of biocompatible resin to form a layer of the resorbable implant and actuating the additive manufacturing apparatus to expose at least some additional amount of biocompatible resin to light to at least partially cure the exposed additional
(Continued)

amount of biocompatible resin to form an additional layer of the resorbable implant and to at least partially overcure previously cured layers to cause at least some interlayer binding between the previously cured layers and the additional layer.

19 Claims, 6 Drawing Sheets

(51) Int. Cl.
  *A61L 27/56* (2006.01)
  *G02B 26/08* (2006.01)
  *A61L 27/60* (2006.01)

(58) Field of Classification Search
  USPC .................................... 264/401, 494, 496
  See application file for complete search history.

(56) References Cited

U.S. PATENT DOCUMENTS

| | | | |
|---|---|---|---|
| 4,996,010 A | 2/1991 | Modrek | |
| 5,096,530 A * | 3/1992 | Cohen | B29C 67/0074 118/506 |
| 5,274,565 A | 12/1993 | Reuben | |
| 5,357,429 A | 10/1994 | Levy | |
| 5,522,019 A | 5/1996 | Bala et al. | |
| 5,554,190 A | 9/1996 | Draenert | |
| 5,647,018 A | 7/1997 | Benjamin | |
| 5,682,886 A | 11/1997 | Delp et al. | |
| 5,741,215 A | 4/1998 | D'Urso | |
| 5,752,962 A | 5/1998 | D'Urso | |
| 5,768,134 A | 6/1998 | Swaelens et al. | |
| 5,813,984 A | 9/1998 | Haaga et al. | |
| 5,871,018 A | 2/1999 | Delp et al. | |
| 6,071,982 A | 6/2000 | Wise et al. | |
| 6,124,373 A | 9/2000 | Peter et al. | |
| 6,126,690 A | 10/2000 | Ateshian et al. | |
| 6,146,390 A | 11/2000 | Heilbrun et al. | |
| 6,205,411 B1 | 3/2001 | DiGioia, III et al. | |
| 6,206,927 B1 | 3/2001 | Fell et al. | |
| 6,254,639 B1 | 7/2001 | Peckitt | |
| 6,261,493 B1 | 7/2001 | Gaylo et al. | |
| 6,327,491 B1 | 12/2001 | Franklin et al. | |
| 6,415,171 B1 | 7/2002 | Gueziec et al. | |
| 6,445,943 B1 | 9/2002 | Ferre et al. | |
| 6,459,948 B1 | 10/2002 | Ateshian et al. | |
| 6,470,207 B1 | 10/2002 | Simon et al. | |
| 6,500,378 B1 * | 12/2002 | Smith | B29C 35/08 264/308 |
| 6,849,223 B2 * | 2/2005 | Dean | A61F 2/28 156/272.8 |
| 6,923,817 B2 | 8/2005 | Carson et al. | |
| 6,937,696 B1 | 8/2005 | Mostafavi | |
| 7,747,305 B2 | 6/2010 | Dean et al. | |
| 2001/0027271 A1 | 10/2001 | Franck et al. | |
| 2002/0059049 A1 | 5/2002 | Bradbury et al. | |
| 2002/0123817 A1 | 9/2002 | Clasbrummel et al. | |
| 2003/0013080 A1 | 1/2003 | Luebke et al. | |
| 2003/0216669 A1 | 11/2003 | Lang et al. | |
| 2004/0054372 A1 | 3/2004 | Corden et al. | |
| 2004/0167390 A1 | 8/2004 | Alexander et al. | |
| 2005/0239971 A1 | 10/2005 | Husler et al. | |
| 2006/0039939 A1 | 2/2006 | Lai et al. | |
| 2007/0154558 A1 | 7/2007 | Gaserod et al. | |
| 2008/0015433 A1 | 1/2008 | Alexander et al. | |
| 2008/0315461 A1 * | 12/2008 | Henningsen | B29C 67/0055 264/401 |
| 2009/0130174 A1 | 5/2009 | Guelcher et al. | |
| 2009/0130449 A1 | 5/2009 | El-Siblani | |
| 2010/0262272 A1 * | 10/2010 | Shkolnik | B29C 67/0088 700/120 |
| 2012/0010711 A1 | 1/2012 | Antonyshyn et al. | |
| 2012/0072185 A1 | 3/2012 | Lang et al. | |

OTHER PUBLICATIONS

Armentano, et al., "Biodegradable polymer matrix nanocomposites for tissue engineering: A review, 95 Polymer Degradation and Stability," vol. 95, pp. 2126-2146, Jun. 18, 2010.

Peter, "Injectable in situ polymerizable, biodegradable scaffolds based on poly (propylene fumarate) for guided bone regeneration," Ph.D Thesis, Rice University, Chapters 1.2 and 2, 1998.

International Search Report and Written Opinion of corresponding International Application No. PCT/US2011/048620, dated Apr. 10, 2012.

International Preliminary Report on Patentability of corresponding International Application No. PCT/US2011/048620, dated Feb. 26, 2013.

Zachow S. et al., "Optimized arrangement of osseointegrated implants: a surgical planning system for the fixation of facial prostheses" Proceedings of 13th International Symposium on Computer Assisted Radiology and Surgery (Cars '99), Paris, France, Jun. 23-26, 1999, pp. 942-946, XP001011404 1999,Amsterdam, Netherlands, Elsevier Science, Netherlands ISBN: 0-444-50290-4 (previously cited in U.S. Appl. No. 10/129,308, filed Sep. 3, 2002).

Noordmans H.J. et al., "Localisation of subdural EEG electrode bundles in an interactive volume rendering framework" Medical Image Computing and Computer-Assisted Intervention—Miccai '99, Second International Conference, Proceedings (Lecture Notes in Computer Science vol. 1679),-Cambridge, UK, Sep. 19-22, 1999, pp. 734-741,XP0010113911999, Berlin, Germany, Springer-Verlag, Germany, ISBN: 3-540-66503-X, abstract (previously cited in U.S. Appl. No. 10/129,308, filed Sep. 3, 2002).

Wells W.et al., "Video Registration Using Fiducials for Surgical Enhanced Reality" Proceedings of the Annual International Conference of the Engineering in Medicine and Biology Society, US, New York, IEEE, vol. Conf. 15, Oct. 28, 1993 (Oct. 28, 1993), pp. 24-25, XP000431483 (previously cited in U.S. Appl. No. 10/129,308, filed Sep. 3, 2002).

Article entitled "Biomedical applications" found at http:\\www.ifi.unizh.ch/staff/zolli/cap/biomedical.htm.

Dean H.D. et al., "Comparison of Traditional Brain Segmentation Tools with 3D Self-Organizing Map".

Sailerh.F. et al., "The value of stereolithographic models for preoperative diagnosis of craniofracial deformities and planning of surgical corrections," Int. J. Oral Maxillofac, Surg. 1998, 27, 327-333 ISSN 0901-5027.

* cited by examiner

CONTINUOUS DIGITAL LIGHT PROCESSING ADDITIVE MANUFACTURING OF IMPLANTS

CROSS REFERENCE TO RELATED APPLICATIONS

This application claims the benefit of U.S. Provisional Patent Application Nos. 61/373,353 filed on Aug. 20, 2010 and 61/491,194 filed on May 29, 2011, which are incorporated herein by reference.

GOVERNMENT LICENSE RIGHTS

This invention was made with government support under grant number R01-DE013740 awarded by the National Institutes of Health (NIH). The government has certain rights in the invention.

BACKGROUND

Implants may be designed to match a defect in a patient's tissue. The shape of the implant may be determined by first measuring the defective area or volume within the patient. The implant may then be designed by, for example, computer aided design (CAD) in light of the measured defective area or volume. The implant may then be manufactured.

Factors to take into account when designing and manufacturing implants include adequate geometry to provide a proper fit within the patient and, in the case of tissue engineering scaffolds, to facilitate host tissue growth and vascular infiltration.

Functional geometrical features of a scaffold may be designed to affect cell attachment, proliferation, or maturation. Surface features that interact directly with cells include scaffold roughness and porosity. Rough, porous structures may facilitate cell loading, neotissue growth, and host tissue ingrowth. The designer may manipulate porous geometry to control both the mechanical properties of the whole implant as well as the pore space's porosity, tortuosity, permeability, and total pore volume. Many tissue engineering scaffolds may require pores that range between 200 and 1600 micrometers with surface features, such as the shape of the pore opening, in the order of 50-500 micrometers. Conventionally, these features may have been obtained, if at all, by the inclusion of particles such as tricalcium phosphate crystals into the resin from which the scaffold would be manufactured. However, concerns may arise as to the resorbability of the crystals in the host's body.

Another important geometrical feature may be oblique orientation of pore structures for the host tissue to not encounter a wall or barrier in the scaffold, which is more likely when pore structures are built orthogonally than when pores or channels are oriented towards host tissue. The implant designer may want to orient pores channels within a scaffold so that they open toward the host tissue thereby facilitating growth of new tissue into the implant and active incorporation of the implant into the host tissue.

Additive manufacturing of implants or scaffolds with these mechanical and geometrical features requires relatively high accuracy levels. For example, accurate rendering makes it more likely that complex internal pore structures such as those described above and other can be created.

Additional factors to take into account when designing and manufacturing implants or scaffolds are adequate strength and stiffness for the part to handle and transmit mechanical stress. In some cases, strength and stiffness must be weighed against the need for the implant or scaffold to be resorbable or capable of breaking down in the host's body. Manipulation of the polymer's molecular weight often adjusts resorption levels versus strength of the implant, with higher molecular weights often being stronger and lower molecular weights often being more resorbable. However, post-curing handling of low molecular weight scaffolds or implants could be problematic and thus the ideal rendering method would minimize any post-curing handling necessary.

While stereolithographic rendering of implants and scaffolds has been demonstrated, limitations in the commercially available devices result in relatively low accuracy levels.

For example, accuracy and resolution of conventional stereolithographic rendering devices may not allow the devices to produce scaffold or implant surface features such as pores and pore openings at the low end of the optimum geometry scale. And while, conventional stereolithographic rendering devices may be able to produce orthogonally oriented pore structures in implants and scaffolds, they may provide insufficient resolution to produce obliquely oriented pores.

Moreover, stereolithographic rendering may also have various other limitations in the context of manufacturing of implants or scaffolds.

For example, conventional stereolithography devices use a laser to polymerize layers. The laser points downward at the top of a vat of liquid polymer. An elevator sits inside the vat and pulls the part downward as it is rendered, layer by layer. The drawing speed is typically not fast enough to simultaneously draw all pixels in the layer, which may make it difficult to control overcuring or stitching between layers as the implant or scaffold is rendered.

Also, conventional stereolithography devices may not provide a way to modulate the amount of energy at one spot versus another within a layer to, for example, control the depth of polymerization and level or strength of overcuring.

Moreover, conventional stereolithography devices may require use of a wiper blade to smooth the resin between each layer to provide a flat surface. Highly viscous polymers may present reliability issues to this flattening tool.

Additionally, stereolithographic polymerization of resorbable polymer scaffolds using low molecular weight polymers presents challenges. Conventional stereolithographic rendering devices often require post-rendering handling to complete curing of the scaffold or implant, which might be very difficult and may result in distortion or destruction of the low molecular weight polymer scaffold or implant.

BRIEF DESCRIPTION OF THE DRAWINGS

The accompanying drawings, which are incorporated in and constitute a part of the specification, illustrate various example systems, methods, and so on, that illustrate various example embodiments of aspects of the invention. It will be appreciated that the illustrated element boundaries (e.g., boxes, groups of boxes, or other shapes) in the figures represent one example of the boundaries. One of ordinary skill in the art will appreciate that one element may be designed as multiple elements or that multiple elements may be designed as one element. An element shown as an internal component of another element may be implemented as an external component and vice versa. Furthermore, elements may not be drawn to scale.

DETAILED DESCRIPTION

Continuous Digital Light Processing

Figure 1:
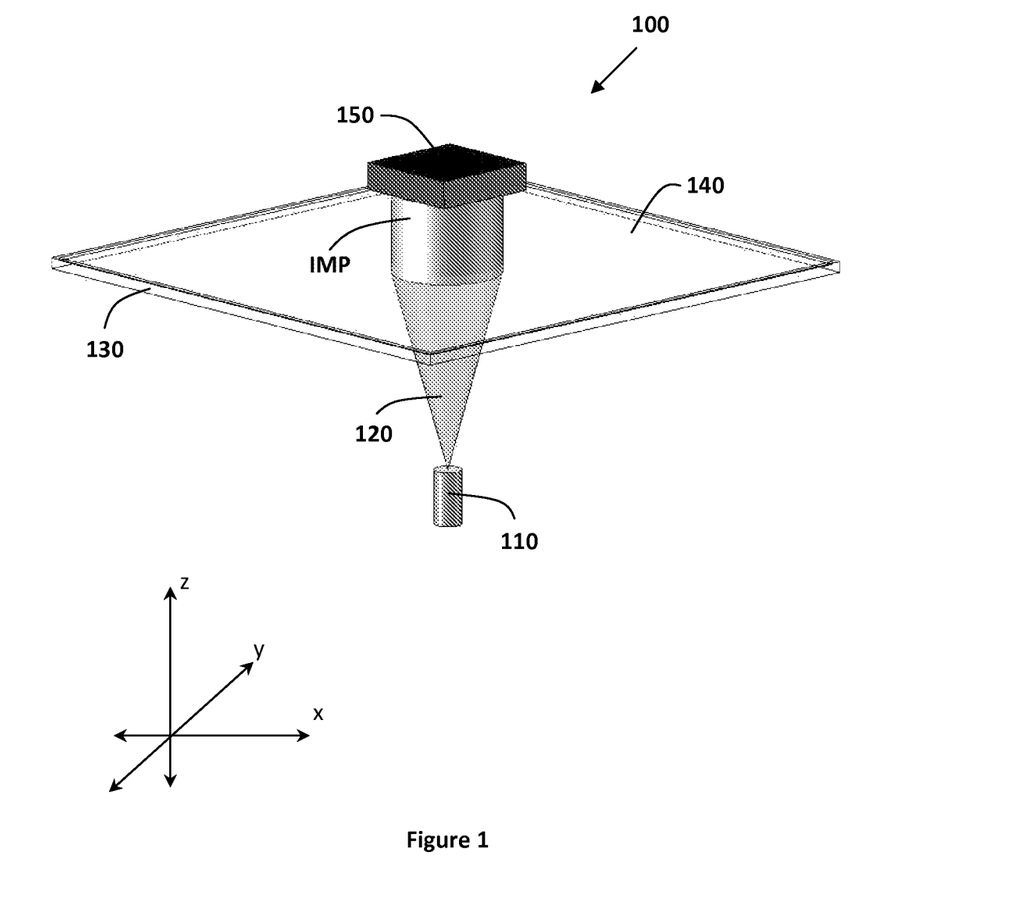
FIG. 1 illustrates a continuous digital light processing (cDLP) device for the additive manufacturing of an implant.

FIG. 1 illustrates a continuous digital light processing (cDLP) device 100 for the additive manufacturing of an implant IMP. The device 100 includes a digital micro-mirror device (DMD) projector 110. A DMD consists of an array of micro-mirrors which controls the intensity of projected light in each pixel of the layer image, effectively polymerizing each voxel (volumetric pixel) of each layer of the implant IMP. The term "continuous" in continuous digital light processing indicates that all voxels within a layer can be projected simultaneously, as opposed to the successive drawing (i.e., moving of laser beam) of voxels that occurs in other additive manufacturing methods such as stereolithography. cDLP based additive manufacturing projects multiple voxels that may add up to a complete implant layer as one image, or "voxel mask." This allows for the entire layer to be cured simultaneously (i.e., continuous curing).

The projector 110 projects light 120 through a transparent or translucent basement plate 130 above which is a resin 140 including a liquid light-polymerizable material. Exposure to the light 120 causes the resin 140 to at least partially cure or polymerize to form layers of the implant IMP. In the illustrated embodiment, the device 100 further includes a build plate 150 to which the implant IMP operatively attaches. The build plate 150 operatively attaches to a motor (not shown), the operation of which successively shifts or elevates the build plate 150 away from the basement plate 130 as the light 120 successively cures or polymerizes the resin 140 to form each layer of the implant IMP. The light 120 further polymerizes or overcures previously rendered layers to bind or stitch newly polymerized layers to the previous layers.

In one embodiment, the cDLP device 100 is the Perfactory® UV device produced by envisionTEC (Gladbeck, Germany). In another embodiment, the cDLP device 100 would be a cDLP device other than the Perfactory® UV device produced by envisionTEC.

Accuracy and Resolution

In one embodiment, each projected voxel mask also uses spatially varying irradiance, meaning that each pixel may be assigned a different light intensity value. Benefits of assigning each pixel a different intensity value include the ability of varying curing rates within a layer and allowing for anti-aliasing methods analogous to those found in image processing. In one embodiment, the cDLP device 100 is equipped with an Enhanced Resolution Module (ERM) (not shown) which effectively doubles the within-layer (x-y) resolution through a process similar to pixel shifting, a technique which increases the true resolution of devices by moving the micro-mirrors by fractions of a pixel in the x and y directions.

The unique properties of cDLP rendering allow for improved accuracy defined as the similarity of the resulting implant or scaffold to the shape found in the design, or CAD, file. One source of increased accuracy is in-plane (x-y) resolution, which is a function of the projector lens magnification and the resolution of the DLP® chip. Pixel sizes may be 75 micrometers or less. ERM, pixel shifting, anti-aliasing, or combinations thereof may further increase the in-plane resolution by at least a factor of 2.

The cDLP device 100 further provides increased accuracy due to increased between-plane or (z) resolution. The between-plane (z) resolution is controlled by, among other factors, the motor (not shown), which shifts the build plate 150 between serial layers. In one embodiment, the device 100 has a motor capable of increments of 50 micrometers and as small as 15 micrometers. The between-plane (z) resolution may be further controlled by controlling the depth of penetration of the light 120 to limit polymerizing energy into the resin 140 or previously rendered layers of the implant IMP.

A model of the Perfactory® UV device has a motor capable of increments of 50 micrometers and a 60 millimeter lens, providing an in-plane (x-y) native resolution of 71 micrometers and 35.5 micrometers utilizing pixel shifting. Thus this model of the Perfactory® UV device is capable of continuously polymerizing 35.5×35.5×50 um voxels. Another model of the Perfactory® UV device would have a 75 millimeter lens that would provide a 42 micrometer native in-plane (x-y) resolution and 21 micrometers resolution with pixel shifting.

Light-Polymerizable Material

The cDLP process controls mechanical and other properties of the resulting implant IMP, in part, by controlling the molecular weight of the light-polymerizable material. Manipulation of the material's molecular weight adjusts the strength of the resulting implant IMP, with higher molecular weights generally being stronger. Thus, for applications where the implant IMP would bear significant mechanical stress, the light-polymerizable material may be chosen such that the rendered part may adequately handle and transmit the mechanical stress.

In applications such as implants or scaffolds, which are intended for implantation in a patient's body, it is important that components of the implant or scaffold including the light-polymerizable material as well as any initiators, dyes, solvents, and other substances be biocompatible, meaning that the implant poses no substantial risk of injury or toxicity to living cells, tissues, or organs, and poses no substantial risk of rejection by the immune system. In some instances, it is possible to use some non-biocompatible components or processes. However, they would usually be fully removed or rendered biocompatible prior to implantation. For example, some non-biocompatible chemicals may be used during the manufacturing process but be fully removed before implantation.

In applications such as tissue engineering scaffolds, resorbability of the scaffold, the ability of the part to break down in the host's body, is a very important consideration. It is important to the regeneration of tissue such as bone that the scaffold resorb in response to cell maturation and incoming host tissue. Well-timed scaffold resorption is important for successful integration of vasculature to allow unfettered remodeling and host incorporation of neotissue. Thus, predictable scaffold resorption is important including predictable rates of loss of material properties, predictable rates of scaffold degradation (e.g., it may be useful to choose polymers that fracture or erode at predictable rates rather than bulk degrade), and predictable rates pH change.

Strength and stiffness of the scaffold must be weighed against rates of resorbability of the scaffold. Manipulation of the material's molecular weight generally adjusts resorption levels versus strength of the scaffold with higher molecular weights resulting in stronger but less resorbable scaffolds and lower molecular weights resulting in weaker but more resorbable scaffolds.

Low molecular weight polymers are often capable of safely breaking down and be resorbed within the body. In general, resorbable polymers are often of very low molecular weight compared to polymers used in common automotive, aerospace, and industrial applications. Resorbable polymers usually have as low as 2-3 orders of magnitude lower molecular weight than the polymers used in those applications.

In addition to being resorbable, ideally, the resulting implant would have sufficient "green strength" to allow post-rendering cleaning of unpolymerized material from the implant's structure including its pores. Green strength is defined as the strength of the rendered implant immediately after cDLP occurs, but before unpolymerized material is washed out, and before any post-curing such as UV light box exposure or heat-based curing.

In one embodiment, the cDLP process of the present disclosure uses the resorbable polymer poly(propylene fumarate) or PPF as the light-polymerizable material. PPF incorporates most of the characteristics discussed above for the light-polymerizable material including low molecular weight, no toxicity and resorbability. In another embodiment, the cDLP process of the present disclosure uses a resorbable light-polymerizable material other than PPF. In yet another embodiment, the cDLP process of the present disclosure uses a light-polymerizable material that although not resorbable is biocompatible or bioneutral. In one embodiment, the liquid light-polymerizable material has a molecular weight of approximately 4,000 Daltons or less. In another embodiment, the liquid light-polymerizable or light-curable material has a molecular weight of approximately 1,200 Daltons or less. In yet another embodiment, the light-curable material has a molecular weight in the range of 1,000 Daltons and 20,000 Daltons.

Viscosity

Some liquid light-polymerizable materials such as PPF are highly viscous. In cDLP, a missed layer may result if insufficient resin 140 is available above the basement plate 130 or if air bubbles form in that layer due to excessive viscosity of the resin 140 incorporating the liquid light-polymerizable material. Viscous resins may also require a longer pause between layers, as more time is required for the flow into void spaces left in the areas where the previous layer was cured.

Use of a solvent may alleviate these issues by reducing the resin's viscosity. However, the use of a solvent may affect the rigidity of the implant or scaffold, with higher amounts of solvent making the implant less rigid. Ideally the resin's viscosity would be reduced without sacrificing implant rigidity. Moreover, any substance used to reduce the resin's viscosity would have to possess some of the same characteristics described above for the liquid light-polymerizable material including no toxicity.

In one embodiment where the liquid light-polymerizable material used in the resin 140 is PPF, diethyl fumarate (DEF) is added to the resin 140 to reduce the resin's viscosity. DEF is a monomer precursor to PPF. This monomer cross-links into the resulting implant or scaffold and once cross-linked poses little to no toxicity risk. In one embodiment, the proportion of DEF to PPF is 1:1 by weight. In one embodiment, the proportion of DEF to PPF is 1:2 by weight. In one embodiment, the proportion of DEF to PPF is 1:3 by weight. In another embodiment the proportion of DEF to PPF is less than 1:3 by weight. In yet another embodiment, the substance used to reduce the resin's viscosity is a substance other than DEF. In one embodiment, no substance is added to the resin to reduce the resin's viscosity.

Initiator

Photo-initiators are added to the resin including the liquid light-polymerizable material to promote the polymerization reaction. In one embodiment, bis(2,4,6-trimethylbenzoyl) phenylphosphine oxide (BAPO) brand name Irgacure® 819 (BASF (Ciba Specialty Chemicals)) is used as the initiator. In one embodiment, the percentage by weight of initiator in a resin including the liquid light-polymerizable material is in the range of 0.5% and 1.0%. In another embodiment, the percentage by weight of initiator in a resin including the liquid light-polymerizable material is in the range of 1.0-2.0%. In another embodiment, the percentage by weight of initiator in a resin including the liquid light-polymerizable material is in the range of 2.0-3.0%. In other embodiments, the percentage by weight of initiator in a resin including the liquid light-polymerizable material is lower than 0.5% or higher than 3.0%.

Dye

As discussed above, the between-plane (z) resolution of the cDLP process may be further controlled by controlling the depth of penetration of polymerizing light energy into the light-polymerizable material being cured or previously cured implant layers. Some level of light penetration into previously rendered layers may be desired to ensure overcuring or stitching between layers, also known as interlayer binding. However, if light penetrates too deeply, previously cured layers may overcure resulting in undesired characteristics of the resulting implant or scaffold.

A property of the chosen dye to take into consideration is its ability to stay suspended in the resin throughout the rendering process. For some dyes, it may be necessary to stop the process and re-stir the resin if the dye is settling out.

In one embodiment, a dye is added to the resin including the liquid light-polymerizable material to at least in part control the depth of penetration of polymerizing light energy into the scaffold or implant layers and therefore assist in controlling interlayer binding. In one embodiment, the dye possesses some of the same characteristics described above for the liquid light-polymerizable material including no toxicity. For example, dyes such as azo chromium dye that may provide adequate control of the depth of penetration of polymerizing light energy into the scaffold or implant layers may be toxic and thus may not be well suited for implant applications.

Since the dye used in a dye-initiator package is likely to be incorporated into the scaffold, it may be useful to use dyes that could also positively influence scaffold surface roughness, act as a bioactive compound such as an antibiotic, or otherwise affect the scaffold degradation environment (e.g., buffer the pH if it would otherwise be too acidic or basic). In one embodiment, a dye used is doxycycline hyclate. In another embodiment, a dye used is amphotericin B.

In one embodiment, titanium dioxide ($TiO_2$) is added to the resin including the liquid light-polymerizable material as a dye to at least in part control the depth of penetration of polymerizing light energy into the scaffold or implant layers. In another embodiment, a dye other than $TiO_2$ or a combination of dyes including dyes other than $TiO_2$ are added to the resin including the liquid light-polymerizable material to at least in part control the depth of penetration of polymerizing light energy into the scaffold or implant layers. In yet another embodiment, no dye is added to the resin including the liquid light-polymerizable material.

Referring back to FIG. 1, in one embodiment, the DMD projector 110 projects light 120 upward through the basement plate 130 above which is a resin 140 that includes a dye. The dye limits the depth of penetration of the light 120, thereby improving control of the curing depth of each individual voxel. The concentration of dye used can be varied to control the depth of penetration of light 120. The amount of dye present in the resin 140 affects the amount of energy that is imparted to the polymerization reaction.

The dye limits the depth of polymerization allowing for the option of using higher levels of irradiance without losing resolution in the z direction. The current layer may be cured at a high energy level without excessive overcuring of previously rendered layers. The use of higher levels of light energy in this way may increase implant green strength.

Dye-Initiator Package

Figure 2:
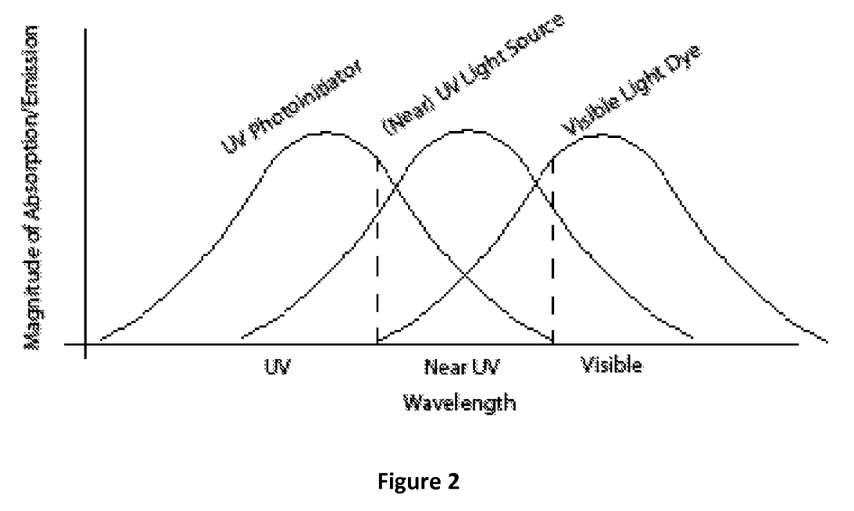
FIG. 2 illustrates an exemplary chart plotting wavelength versus magnitude of light absorption/emission for an initiator, a light source, and a dye.

FIG. 2 illustrates an exemplary chart plotting wavelength versus magnitude of light absorption/emission for the initiator, the light source, and the dye. The primary function of the dye is to block light. For many dyes, this will be accomplished by light absorption. For other dyes, this is accomplished by light reflection or scattering. Thus the dye will compete with the initiator for photons. The area between the lines a and b in FIG. 2 is the area where the cDLP process has the greatest control over depth of light penetration and amount of polymerizing energy imparted to the initiator. Light of a wavelength to the left of line a would not be blocked by the dye. Light of a wavelength to the right of line b would not cause proper polymerization of the resin.

To further reduce the depth of penetration of light, the amount of dye in the resin may be increased. However, it may also be necessary to increase the amount of initiator present as the amount of dye is increased. Thus, the dye and initiator form a "dye-initiator package" because the amount of each included in the resin would depend upon the amount of the other. The chart of FIG. 2 is exemplary and other wavelengths of initiator, light source, or dye could be used resulting in a different chart.

In one embodiment, the dye concentration in the resin is between 1-5% by weight to reduce the depth of penetration of light to approximately 120 micrometers with 50 micrometer layers and 70 micrometers of overcuring to previously rendered layers. In another embodiment, the dye concentration in the resin is between 0.01 and 0.2% by weight in the resin. In another embodiment, the dye concentration in the resin is between 0.2 and 0.5% by weight in the resin. In yet another embodiment, the dye concentration in the resin is lower than 0.01% or higher than 5% by weight. In one embodiment, overcuring of previous layers is selected to be in the range of between 10% and 300%.

Scaffolds

A scaffold design may include an external shape that accurately fits a patient-specific defect site. Moreover, the design may require complex three-dimensional structures.

Figure 3:
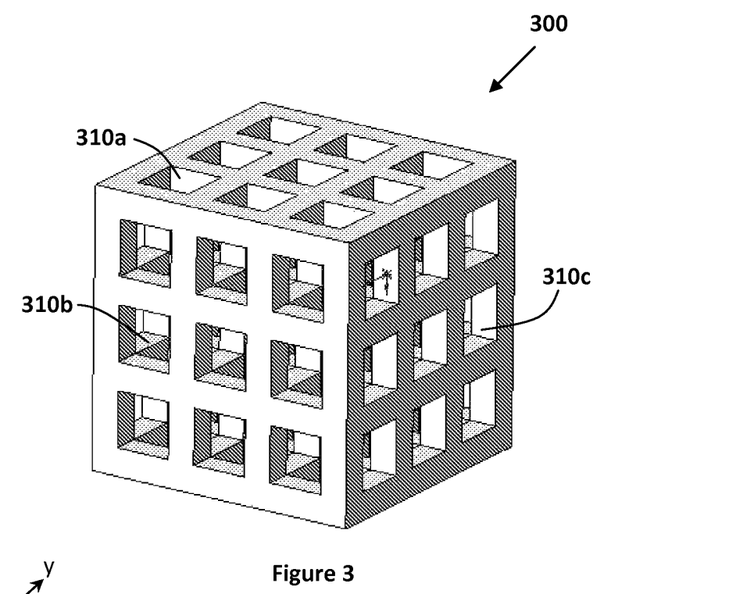
FIG. 3 illustrates an exemplary porous structure scaffold.

FIG. 3 illustrates an exemplary scaffold 300. The scaffold 300 includes pores 310a-c that are orthogonal or at right angles with the layers of the scaffold 300. The three dimensional geometry of scaffolds including internal spaces may be important to the loading of cells and the establishment of vascular channels. In one embodiment, a scaffold includes pores or internal channels. In one embodiment, the diameter of pores and channels in the scaffold is between 150 micrometers and 1 millimeter. In another embodiment, the diameter of pores and channels in the scaffold is between 50 micrometers and 1.6 millimeters. In other embodiments, the diameter of pores and channels in the scaffold is smaller than 50 micrometers or larger than 1.6 millimeters. Modeling of scaffold pores at these ranges may require compensation in the CAD to correct for, among other factors, post-curing shrinkage of implants or swelling due to wetting caused by pre-implantation cell culturing or implantation itself.

In addition to the scaffold design parameters relating to pore size, the design may require complex porous structures that facilitate cell loading, neotissue growth, and host tissue ingrowth. For example, the design may require that pores or channels open toward the host tissue in the defect site to allow tissue ingrowth prior to the implant's full degradation. More accurate rendering makes it more likely that complex internal pore structures can be created.

Figure 4:
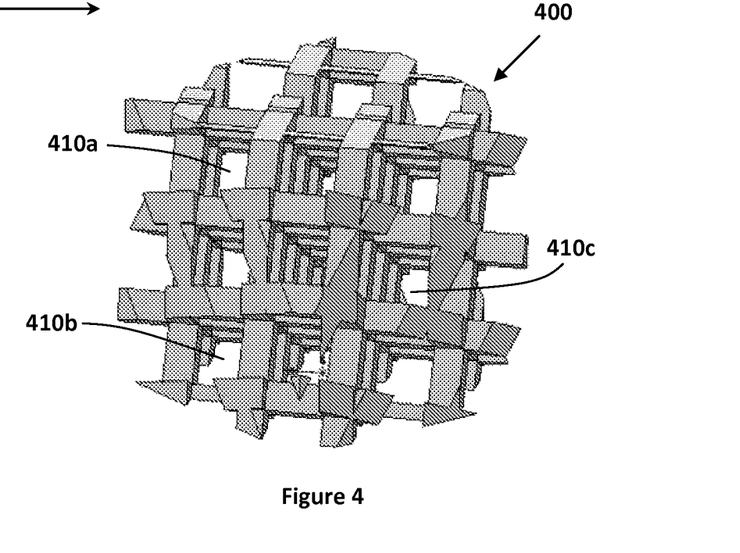
FIG. 4 illustrates an exemplary porous structure including pores that are oblique.

FIG. 4 illustrates an exemplary porous structure scaffold 400. The scaffold 400 includes pores 410a-c that are oblique. Oblique is defined to be any direction that is not parallel to the x, y, and z directions by which scaffolds are rendered using the above described additive manufacturing techniques. Oblique construction may be important to make sure that the host's tissues do not encounter a wall (barrier) in the scaffold, which is more likely when pore structures are built orthogonally than when pores and/or channels are oriented towards the host tissue. The implant designer may want to orient pores and/or channels within a scaffold so that they open toward the host's tissue thereby facilitating growth of new tissue into the implant and active incorporation of the implant into the host's tissues.

Additive manufacturing devices with voxel resolution in the range of 100-1000 micrometers may be able to bring about orthogonally oriented pore structures, however they may provide insufficient resolution to produce obliquely oriented pores in these ranges. Resolution of the cDLP device is such that rendering of structures having obliquely oriented pores is possible.

Additionally, in tissue engineering scaffold applications where an initial goal is cell attachment, PPF's hydrophobic surface can be modified through radiofrequency glow-discharge (RFGD) or by soaking the implant in serum to provide for protein adsorption. Cell attachment can also be mediated by other factors embedded in the surface that mimic extracellular matrix components. This includes surface roughness, which may include indentations and protrusions having diameters ranging from 1 nanometer to 100 micrometers, as well as the material's compliance.

Once attached, the goal is likely to shift to cell proliferation and eventually maturation as host tissue integrates. In addition to the effect the dye has on surface roughness, other compounds, such as tricalcium phosphate crystals, can be added to the resin in the additive manufacturing device. However, as with the dye, depending on solubility, crystal size, and tendency to aggregate, it may be difficult to keep these crystals suspended in the resin at a relatively constant concentration throughout the scaffold rendering process.

Scaffold design features, such as wall thickness, affect the macro strain distribution and may be optimized to resist trauma. Moreover, it may be necessary to counterbalance desired resorption processes with the need for the implant to be loaded during tissue regeneration. The need to localize strain-bearing portions of a scaffold may necessitate the consideration of regions lacking porosity or regions rendered with composite materials, some of which may not degrade.

Post Rendering

Final part accuracy may be dependent upon thorough part cleaning post rendering. This may be necessary to remove any residual uncured resin which would crosslink post rendering. The choice of washing procedures in turn relies on the mechanical integrity of the resin as cured by the cDLP process or green strength. Parts which are accurately rendered but remain soft may become damaged by improper handling or the use of harsh solvents. Once cleaned, final part strength may be improved by post-curing in a UV bath.

Example 1

A first embodiment focused on the calibration of the cDLP additive manufacturing system to accurately render scaffolds with predictable properties of resorption, cell attachment and proliferation, host incorporation, and tissue regeneration.

Figure 5:
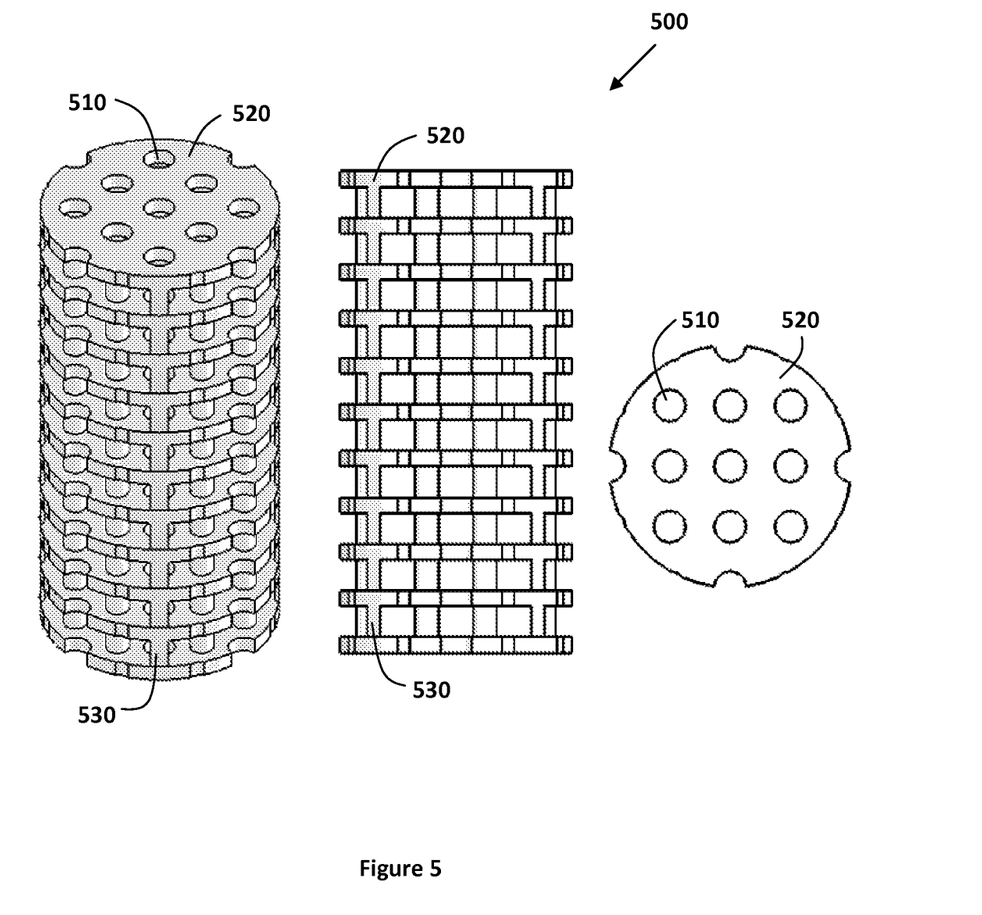
FIG. 5 illustrates isometric, front, and top views of an exemplary scaffold.

FIG. 5 illustrates isometric, front, and top views, respectively, of an exemplary scaffold 500. The goal of the calibration study was to calibrate the cDLP system for the additive manufacturing of scaffolds with the "plate and post" geometry of scaffold 500. In the embodiment, the cylindrical test scaffold was 6.0 millimeters in diameter and 12.4 millimeters in length. The diameter of the vertical channels 510 was 800 micrometers. The plates 520 were 400 micrometers thick and 800 micrometers apart from each other. The posts 530 between the plates, were 600 micrometers in diameter. The calibration of the cDLP process consisted of at least six steps.

The first step in the calibration procedure was to polymerize single layers of the cDLP resin including PPF, DEF, BAPO, and the dye. There are at least three variables to study: dye concentration, initiator concentration, and irradiance duration. Other factors that could be varied would be polymer molecular weight and polydispersity as well as irradiance level (i.e., the amount and rate at which light is applied). The goal was to have a layer thickness that insures adequate overcuring between layers, yet is thin enough to allow for a desired "z" step size and the generation of accurate geometries. Resolution in x, y, and z will determine the accuracy of the desired external and internal pore surface geometry.

The second step was to insure that the material properties of the chosen resin configuration will provide useful scaffolds. In some cases scaffolds will be loaded with cells and/or growth factors and immediately implanted. In other cases scaffolds will be pre-cultured (e.g., in a bioreactor) prior to implantation.

The third step involved the use of the resin to form a "burn-in" patch on the basement plate on the upper elevator of the cDLP device. For this embodiment, we were not able to directly cure a burn-in patch on the build plate. Therefore, the burn-in patch was obtained by overcuring resin on the basement plate. The overcured resin patch was then transferred to the build plate and cured onto that plate using a UV bath (Procure™ 350, 3D Systems) followed by warming with a heat gun. Heat was used to ensure that the patch center cured to the underlying build platform as the dye content of the resin could prevent UV penetration at the patch edges. Care was taken to allow the heated layer and platform to cool to prevent accelerated curing when the patch was reintroduced to the device. This procedure allowed scaffolds to cure to the PPF resin directly, rather than the metal platform itself.

The fourth step involved the transfer of the scaffold CAD file to the cDLP device for rendering. The CAD file may contain support structures spanning the space between the scaffold and the burn-in patch. The support structures rise sufficiently above the burn-in patch to allow resin to circulate between the burn-in patch and the scaffold during rendering of the scaffold and to allow washing out of unpolymerized resin following that procedure.

The fifth step involved rendering the multi-layer scaffold as discussed above.

The sixth step involved testing the scaffolds both in vitro and in vivo. In vitro testing includes mechanical tests, biological environments without cells or tissues, and biological environments with cells, growth factors, and/or tissues.

A 1200 Daltons PPF was prepared, synthesized and purified per known methods. Briefly, DEF (Acros, Pittsburgh, Pa.) and propylene glycol (Acros) were reacted in a 1:3 molar ratio with hydroquinone and zinc chloride as a crosslinking inhibitor and a catalyst, respectively. This reaction created the intermediate, bis(hydroxypropyl) and ethanol as a byproduct. The intermediate was then transesterified under a vacuum to produce poly(propylene fumarate) and propylene glycol as a byproduct. The PPF was then purified and gel permeation chromatography was used to calculate the number average molecular weight (Mn=1200 Da).

R320 titanium dioxide $TiO_2$ (Sachtleben White Plains, N.Y.) which is a 320 nanometer crystal was used. A 133 micrometer layer of PPF 4.8% $TiO_2$ (range tested: 0-4.8%), 2% BAPO (range tested 0.5-2%), 33% DEF (range tested: 33 and 50%), and an irradiance level of 200 mW/dm$^2$ for 300 seconds (60 s and 300 s were tested). A lateral spreading (i.e., in x and y) of polymerization beyond the intended layer boundaries was observed. This area increased most quickly at higher concentrations of $TiO_2$, especially with increased light input at those high dye concentrations. The area of lateral spreading was not as thickly or as strongly cured as the expected area of exposure. In order to quantify this phenomenon, an extra step was added to the normal curing test calibration procedure. In addition to measuring cured layer thickness, i.e. the z dimension, x-y dimensions were also measured.

The curing test procedure used a small square-shaped test pattern of UV exposure. At each $TiO_2$ concentration increment, the length and width of the cured square-shaped thin layer were recorded. Additionally, the length and width of the total cured area, including those areas affected by lateral polymerization, were also measured. With this data, it was possible to calculate the percent overcure. The length and width, or x and y, measurements were averaged for each part, and this process was repeated three times (n=3) for each $TiO_2$ and BAPO concentration.

The first attempt yielded an incomplete build and a membrane of polymerized material that formed on the basement plate. This was corrected by: (1) regularly straining out polymerized resin, (2) regularly cleaning the basement plate, and (3) monitoring the basement plate throughout the 16 hour build cycle. Cleaning unpolymerized polymer from the internal pore space of the scaffolds was a simple procedure using an ultrasonic alcohol bath. The scaffolds rendered were accurate to within 80 micrometer.

Depth of polymerization (micrometers) was characterized as a function of titanium dioxide concentration (wt %) for five different combinations of BAPO concentration (wt %) and exposure time (s). From these tests, it was determined that a 2 wt % titanium dioxide concentration with 2 wt % BAPO and a 60 s exposure time would yield an average depth of polymerization equal to 133.3 micrometers. These settings could therefore be used to build in 50 micrometer layers with 83.3 micrometers of overcuring. A 200 mW/dm$^2$ irradiance was used.

High refractory index of the TiO$_2$ caused light scattering. While this scattering is in all directions rather than only in the z direction, the amount of solid layer curing continued to occur only in the z direction. There was no interlayer overcuring in other directions as there were no additional layers to the sides and the layers above the current location were not yet in existence. Increasing TiO$_2$ concentration led to an increased amount of lateral overcuring. Testing was performed using a 200 mW/dm$^2$ irradiance and a 300 s exposure time. Two levels of BAPO were tested for each titanium dioxide concentration.

The cDLP devices used can provide native accuracies of up to 13 micrometers in z and 71 micrometers in x and y, and up to 35.5 micrometers when using anti-aliasing or pixel shifting software. This is sufficient resolution to prepare patient specific implants. This resolution is high enough that surface features (e.g., surface roughness) could be rendered to ideal scales for cells to respond to.

Using 1200 Daltons PPF, we were able to use a cDLP device to render layers as thin as 60 micrometers. The resulting highly accurate scaffolds are likely to allow improvements in the modeling, prediction, and eventual design of scaffold-specific cell attachment, proliferation, maturation, and resorption parameters. The use of dye-initiator packages allow the production of very highly accurate features with sufficient green strength to allow aggressive postrendering removal of unpolymerized resin and handling.

Example 2

This embodiment was implemented on the Perfactory® UV device having a 60 millimeter lens. A relatively small amount of dye was necessary (for example, 0.01 to 0.2 wt %) of overall resin mass. The dye used in this study was at a greater concentration than is typically used in industrial applications, up to 0.5% of overall polymer mass. It is important that the dye be biocompatible. In this study, a yellow chromium azo dye was used. The amount of initiator used in this study was 2% of Irgacure® 819 (BASF (Ciba), Florham Park, N.J.). The substance used in this study to reduce the viscosity of the resin was diethyl fumarate (DEF), the monomer precursor of PPF.

The designed (i.e., in CAD software) plate thickness and post diameter were 0.4 millimeters and 0.6 millimeters, respectively. The ten-plate scaffolds generated had an average plate thickness of 0.43±0.02 millimeters, and average post thickness of 0.63±0.01 millimeters. The precision of the features (i.e., low standard deviation) may be as important as the high accuracy. These features measured slightly above their designed dimensions. Although the features here were slightly larger than anticipated, there is typically a shrinkage effect which is observed in the curing of photopolymers which results in features which are smaller than as designed. This effect can be resolved in the cDLP system by manipulating the energy distribution for the voxel and the strategy used in the exposure of a single voxel data set. In designing part supports, it is critical to use a support geometry that can distort to prevent anisotropic shrinkage of the scaffold. If the part is firmly attached to the build platform, the base is unable to shrink while the rest of the scaffold shrinks, leading to anisotropy in the amount of deformation. Because one can insure the between-plan dimensions by the physical translation of the build platform and overcuring, only the in-plane dimensions need be corrected (i.e., scaled to correct for shrinkage).

Example 3

For this embodiment, the Perfactory device used had a 60 millimeter lens providing an in-plane native resolution of 71 micrometers and 35.5 micrometers utilizing pixel-shifting. The resorptive polymer, poly(propylene fumarate) (PPF), was used. A yellow chromium azo dye was added. The initiator used in this embodiment was Irgacure® 819 (BASF (Ciba), Florham Park, N.J.). The substance used to reduce the viscosity of the PPF was diethyl fumarate, the monomer precursor of PPF. The between plane energy settings were calibrated to achieve a voxel height of 120 micrometers when using a 200 mW/dm$^2$ irradiance, and an exposure time of 120-240 s. The scaffold shape was composed in a Computer Aided Design (CAD) program and 6 scaffolds were rendered using a 120 s exposure. 2 scaffolds were later rendered using a 240 s exposure. 10 measurements of the overall diameter of each scaffold were collected using calipers. The intended scaffold diameter was 6 mm.

The scaffolds (n=6) rendered using the 120 s exposure had the following diameters: 5.83±0.03, 5.83±0.03, 5.85±0.04, 5.82±0.02, 5.83±0.02, and 5.85±0.03 mm. The scaffolds (n=2) rendered using the 240 s exposure had the following diameters: 6.03±0.03 and 6.02±0.02 mm. The 240 s exposure results, showed less shrinkage than the 120 s exposure parts.

Example 4

A Perfactory UV device was used to render porous cylindrical PPF scaffolds with a diameter of 6 millimeters and a length of either 1.2 millimeters (N=10) or 12.4 millimeters (N=8) with either 2 or 4 minute exposure using a "plate and post" geometry. The Computer Aided Design for this scaffold was rendered in 50 micrometers thick layers with a 120 micrometers curing depth to insure sufficient overcuring (inter-layer binding). A yellow chromium azo dye, Irgacure® 819 (BASF [Ciba], Florham Park, N.J.) initiator, and diethyl fumarate were added to the primary material, PPF, and used for scaffold production. A 500-195-20 Mitutoyo (Aurora, Ill.) caliper was used to measure scaffold features. The 12.4 millimeters scaffolds were micro-CT scanned. The 1.2 millimeters scaffolds were imaged via scanning electron microscope (SEM).

Qualitative analysis of micro-CT images presented anisotropic but predictable shrinkage. Qualitative analysis of SEM images presented thinning at layer margins. The 1.2 millimeters scaffolds presented an average observed post diameter (expected 0.4 mm) of 0.43 millimeters (0.02 std dev) and an average observed plate diameter (expected 0.6 mm) of 0.63 millimeters (0.01 std dev). The 12.4 millimeters (4 min exposure group) presented an average diameter (expected 6 mm) of 6.03 millimeters (0.03 std dev). Accurate calibration of overcuring insures interlayer binding and full formation of the smallest, 400 micrometers in this study, scaffold features.

Example 5

Poly(propylene fumarate) (PPF) with an average molecular weight (Mn) of 1200 Daltons was synthesized using the two step process described above. DEF was added in a ratio of 1 g DEF/2 g PPF to lower the viscosity of the material. The photoinitiator BAPO (BASF (Ciba), Ludwigshafen, Germany) was added in a concentration of 5, 10 or 20 mg/g of combined PPF/DEF resin mass. The titanium dioxide concentrations utilized during calibration varied from 0-48 mg $TiO_2$/g of PPF/DEF. Rutile titanium dioxide with an average particle size of 300 nm (Sachtleben, Duisburg, Germany) was used. In combining the components listed here, a particular order was useful to expedite the mixing process and more quickly achieve homogeneity of the resin. BAPO was first added to DEF, which is of much lower viscosity than PPF, and was mixed until thoroughly dissolved. The PPF was then heated to lower its viscosity before adding the DEF/BAPO mixture. Care was taken to avoid excessive temperatures (>70° C.) which could cause the polymer to crosslink. Once the PPF/DEF/BAPO mixture was prepared, $TiO_2$ was added in incremental steps to allow for calibration of curing parameters as a function of T $TiO_2$ concentration.

The cDLP-based additive manufacturing device used for this study was the Perfactory® Mini Multi Lens (envisionTEC, Ferndale, Mich.), which was operated in UV mode. Curing tests were performed to determine the relationship between $TiO_2$ concentration and cured layer thickness. To perform each test, a few drops of resin were placed on a glass slide. The Perfactory device was used to cure the resin with a fixed irradiance and time using a square-shaped test pattern. A 200 mW/dm$^2$ irradiance was used for these tests, and care was taken to calibrate for the added thickness of the glass slide. An exposure time of either 60 or 300 s was used. After the specified time period had elapsed, the excess uncured polymer was removed from the slide leaving only the solid square test pattern. A razor blade was used to remove the thin layer from the slide, and digital calipers were used to measure the thickness of the layer. Three replicates were performed for each unique combination of BAPO and $TiO_2$ concentration evaluated.

Example 6

Resin was prepared using a 1 g DEF/2 g PPF ratio. 20 mg BAPO/g resin and 10 mg $TiO_2$/g resin were used. A successful build required proper attachment of the cured resin to the build plate as the initial layers are cured. Some difficulty was encountered in achieving attachment between the PPF resin and the build platform using industry standard methods, and some intervention was required. A thin base plate was first rendered using two 50 micrometers layers, which did not attach properly to the build platform but rater remained fixed to the transparent basement. The thin plate was carefully removed from the basement using a razor blade and placed directly onto the center of the build platform outside of the Perfactory device. Care was taken to remove any air trapped between the base plate and the platform. The base plate was then cured for 20 minutes in a UV bath. In addition to UV exposure, a heat gun was used to finalize the curing of the base plate in order to achieve a strong bond to the build platform. Providing a preattached base plate generated from PPF resin provided proper attachment of the desired parts during the subsequent build. Once this step was completed, the test scaffolds were built using a 200 mW/dm$^2$ irradiance and a 150 s exposure time.

Some post-processing of the test parts was necessary. The test parts were rinsed first with acetone and then with 200 proof ethanol to remove any excess uncured resin from the internal pore spaces. Compressed air was also used to clean the test scaffolds. Once the parts were free of uncured resin, the build platform was placed in a UV bath and 2 hrs of additional exposure were applied to fully cure the resin and strengthen the parts. The base plate was then separated from the build platform, and the individual test scaffolds were removed from the base plate. The scaffold supports were removed using a razor blade.

The resin used to render the full scaffolds was thinned by adding DEF to increase the concentration to 1:1 PPF/DEF. This was necessary as the resin viscosity had increased due to autopolymerization of the material. The BAPO and $TiO_2$ concentrations were effectively reduced in this process to 15 mg BAPO/g resin and 0.75 mg $TiO_2$/g resin. A pre-attached base plate was used as described above. Scaffolds were rendered using a 200 mW/dm$^2$ irradiance and a 150 s exposure time. After the build process completed, the scaffolds were removed from the build platform and rinsed with 200 proof ethanol. Additional cleaning involved alternating steps of ethanol rinsing, the use of compressed air, and ultrasonic cleaning in ethanol. The use of acetone was avoided as it was found to damage test scaffolds. Once the excess resin had been removed from the scaffolds, they were placed in a UV bath for 2 hrs. The scaffold supports were removed using a razor blade.

Bone marrow was obtained from adult, human volunteers. Primary cultures of isolated hMSCs were seeded. The primary isolates of hMSCs were sub-cultured at a density of 250,000 per culture flask. The hMSCs were trypsinized. Cells were counted and dense cell infusate was prepared at 32.5 million cells/2 ml for seeding of scaffolds. Four PPF scaffolds were rendered, sterilized with ethylene gas oxide (140° F.), and pre-wetted by immersion in 10% fetal bovine serum for 12 hours. The number of hMSCs loaded in each scaffold was 3.25 million (the optimal cells seeding density was based on estimated cell diameter and scaffold surface area). The 2004 of hMSC infusate was layered onto the scaffolds in a multi-well plate (low-attachment plastic) with micropipette. The plate was placed in a vacuum chamber which was rapidly pumped down to 25" Hg for 1 min. The scaffolds loaded with high density cell-infusate were then incubated for two hours to facilitate cell attachment.

At the end of two hours the wells were filled with culture medium (DMEM-LG with 10% fetal bovine serum) to prevent drying. The scaffolds were harvested sequentially at four time intervals: 6, 24, 30 and 48 hours. All the scaffolds were fixed with 1% glutaraldehyde solution for 30 minutes and then rinsed with and stored in phosphate buffered saline (PBS) at 4 degree centigrade for Scanning Electron Microscopy (SEM).

Figure 6:
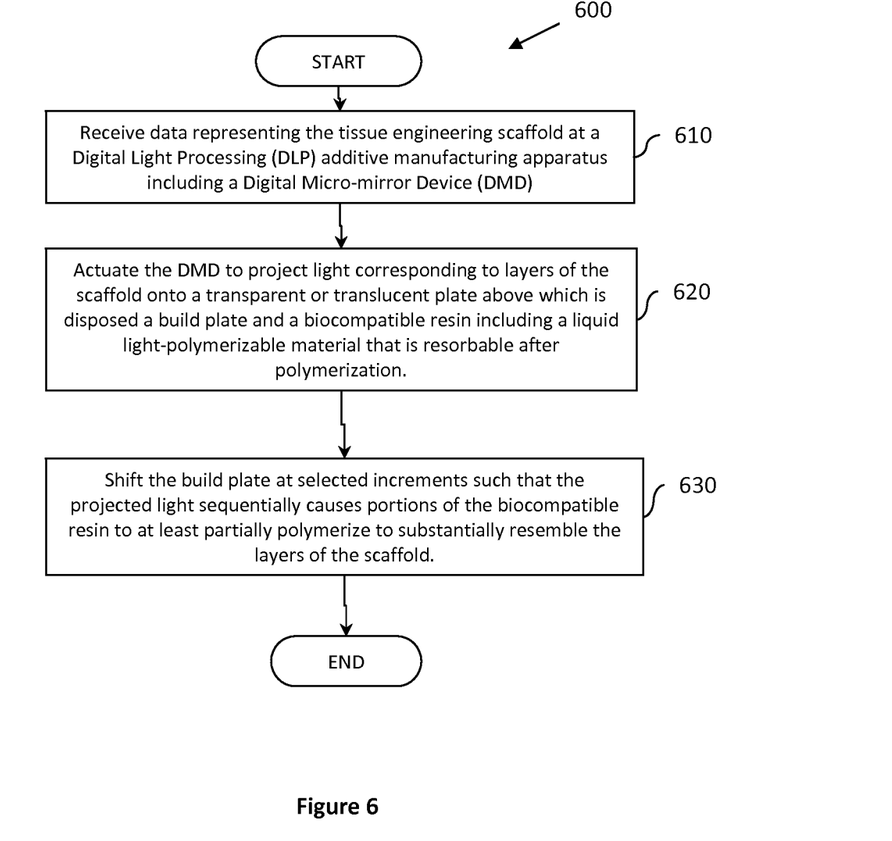
FIG. 6 illustrates a method of manufacturing a tissue engineering scaffold for implantation in a patient and promoting tissue growth.
Figure 7:
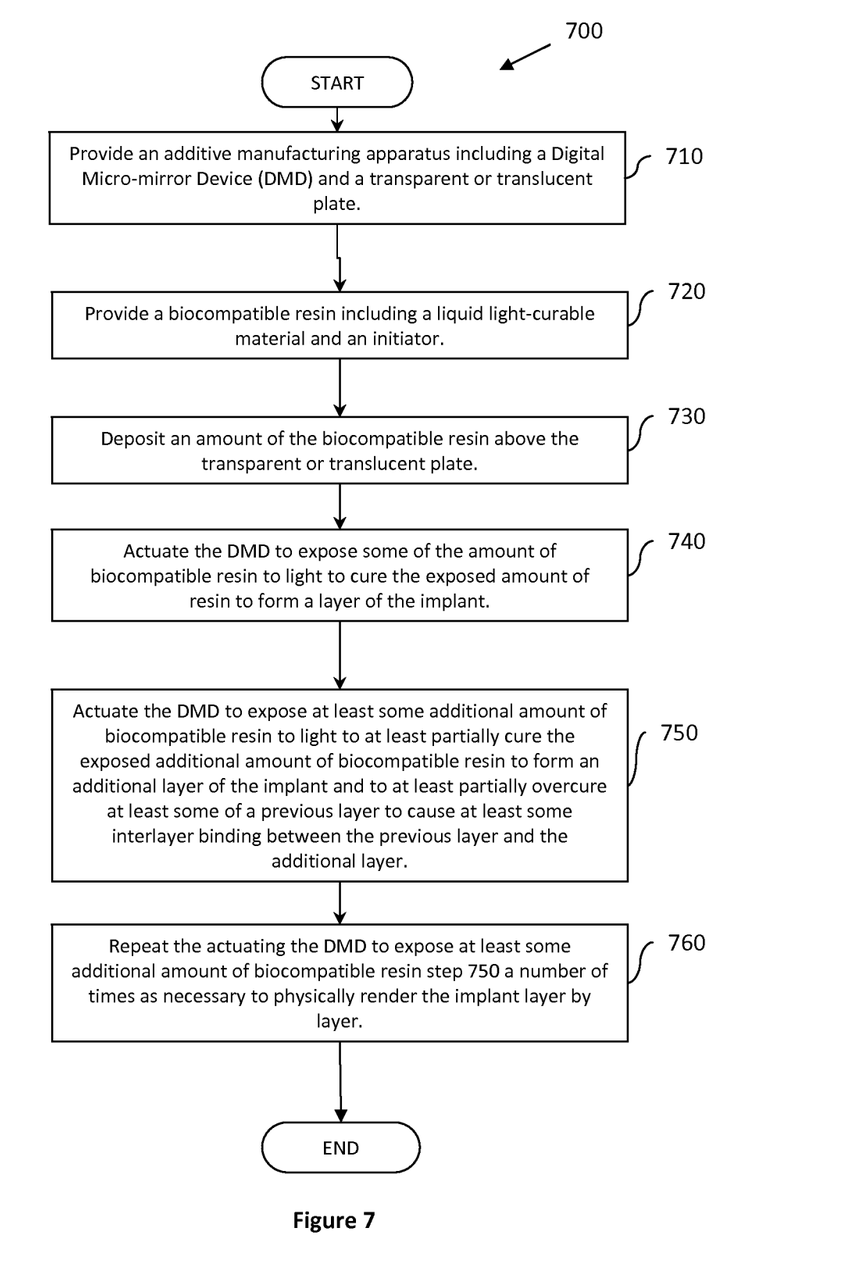
FIG. 7 illustrates a process for continuous digital light processing manufacturing of an implant to be implanted into a patient.

Example methods may be better appreciated with reference to the flow diagrams of FIGS. 6 and 7. While for purposes of simplicity of explanation, the illustrated methodologies are shown and described as a series of blocks, it is to be appreciated that the methodologies are not limited by the order of the blocks, as some blocks can occur in different orders or concurrently with other blocks from that shown or described. Moreover, less than all the illustrated blocks may be required to implement an example methodology. Furthermore, additional or alternative methodologies can employ additional, not illustrated blocks. While FIGS. 6 and 7 illustrate various actions occurring in serial, it is to be appreciated that various actions illustrated could occur substantially in parallel. While a number of processes are described, it is to be appreciated that a greater or lesser number of processes could be employed.

FIG. 6 illustrates a method 600 of manufacturing a tissue engineering scaffold for implantation in a patient and promoting tissue growth. The method 600 includes, at 610, receiving data representing the tissue engineering scaffold at a Digital Light Processing (DLP) additive manufacturing apparatus including a Digital Micromirror Device (DMD). At 620, the method 600 further includes actuating the DMD to project light corresponding to layers of the scaffold onto a transparent or translucent plate above which is disposed a build plate and a biocompatible resin including a liquid light-polymerizable material that is resorbable after polymerization. At 630, the method 600 further includes shifting the build plate at selected increments such that the projected light sequentially causes portions of the resin to at least partially polymerize to substantially resemble the layers of the scaffold.

FIG. 7 illustrates a process 700 for continuous digital light processing (cDLP) manufacturing of an implant to be implanted into a patient. The process 700 includes, at 710, providing an additive manufacturing apparatus including a Digital Micromirror Device (DMD) and a transparent or translucent plate. At 720, the process 700 further includes providing a biocompatible resin including a liquid light-curable material and an initiator. At 730, the process 700 further includes depositing an amount of the resin above the transparent or translucent plate. At 740, the process 700 further includes actuating the DMD to expose some of the amount of resin to light to cure the exposed amount of resin to form a layer of the implant. In one embodiment (not shown), the process 700 further includes shifting the rendered layer of the implant and depositing an additional amount of the resin above the transparent or translucent plate.

At 750, the process 700 further includes actuating the DMD to expose at least some additional amount of resin to light to at least partially cure the exposed additional amount of resin to form an additional layer of the implant and to at least partially overcure at least some of a previous layer to cause at least some interlayer binding between the previous layer and the additional layer. In one embodiment, the process 700 further includes shifting additional layers of the implant before depositing subsequent additional amounts of resin above the transparent or translucent plate, wherein at least one motor in the additive manufacturing apparatus causes the shifting to occur at increments of 75 micrometers or less. At 760, the process 700 further includes repeating the actuating the DMD to expose at least some additional amount of resin step 750 a number of times as necessary to physically render the implant layer by layer.

While example systems, methods, and so on, have been illustrated by describing examples, and while the examples have been described in considerable detail, it is not the intention to restrict or in any way limit the scope of the appended claims to such detail. It is, of course, not possible to describe every conceivable combination of components or methodologies for purposes of describing the systems, methods, and so on, described herein. Additional advantages and modifications will readily appear to those skilled in the art. Therefore, the invention is not limited to the specific details, and illustrative examples shown or described. Thus, this application is intended to embrace alterations, modifications, and variations that fall within the scope of the appended claims. Furthermore, the preceding description is not meant to limit the scope of the invention. Rather, the scope of the invention is to be determined by the appended claims and their equivalents.

To the extent that the term "includes" or "including" is employed in the detailed description or the claims, it is intended to be inclusive in a manner similar to the term "comprising" as that term is interpreted when employed as a transitional word in a claim. Furthermore, to the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

What is claimed is:

1. A method of manufacturing a tissue engineering scaffold for implantation in a patient and promoting tissue growth, the method comprising:
   receiving data representing at least the tissue engineering scaffold at a Digital Light Processing (DLP) additive manufacturing apparatus including a Digital Micromirror Device (DMD);
   actuating the DMD to project light corresponding to layers of the scaffold onto a transparent or translucent plate above which is disposed a build plate and a biocompatible resin including a liquid light-polymerizable material that is resorbable after polymerization, wherein the resin includes a dye and an initiator;
   shifting the build plate at selected increments such that the projected light sequentially causes portions of the resin to at least partially polymerize to substantially resemble the layers of the scaffold; and
   controlling depth of penetration of the projected light by selecting the ratio of the dye to the initiator in the biocompatible resin so that the projected light overcures a previously at least partially polymerized layer, wherein the ratio of dye to initiator is selected to control light penetration such that overcuring of at least one previously rendered layer is in a range between 10% and 300% of layer thickness.

2. The method of claim 1, wherein the produced scaffold includes pores having openings with diameters in the range of 50 to 1600 micrometers.

3. The method of claim 1, wherein the polymerization produces the scaffold to include pores that are oblique.

4. The method of claim 1, wherein the polymerization produces the scaffold to have at least one surface that has formed thereon indentations and protrusions having diameters ranging from 1 nanometer to 100 micrometers.

5. The method of claim 1, wherein the polymerization produces the scaffold to include at least one surface that has at least one of indentations and protrusions having diameters ranging from 1 nanometer to 100 micrometers.

6. The method of claim 1, wherein the liquid light-polymerizable material has a molecular weight of approximately 4,000 Daltons or less.

7. The method of claim 1, wherein the liquid light-polymerizable material has a molecular weight of approximately 1,200 Daltons or less.

8. The method of claim 1, wherein the liquid light-polymerizable material is poly(propylene fumarate) (PPF).

9. The method of claim 1, wherein the resin includes at least one of a bioactive compound and an antibiotic.

10. The method of claim 1, wherein the actuating the DMD to project light simultaneously projects all pixels in an entire voxel data set representing a complete layer of the scaffold.

11. The method of claim 10, wherein the actuating the DMD to project light simultaneously projects at least a first pixel at a different intensity or irradiance than a second pixel.

12. The method of claim 1, wherein the actuating the DMD to project light projects pixels having at least one dimension of 75 micrometers or less.

13. The method of claim 1, wherein the shifting the build plate at selected increments elevates the build plate at increments of 50 micrometers or less.

14. The method of claim 1, wherein the ratio of dye to initiator is selected to control light penetration such that overcuring of at least one previously rendered layer is in at least one of a range between 10% and 50% and a range between 40% and 100% of layer thickness.

15. The method of claim 1, wherein the actuating the DMD to project light includes projecting light at an elevated level of irradiance to increase scaffold green strength.

16. The method of claim 1, wherein the initiator is bis(2,4,6-trimethylbenzoyl)phenylphosphine oxide (BAPO).

17. The method of claim 1, wherein the dye is titanium dioxide (TiO2).

18. The method of claim 1, wherein the resin further includes a solvent.

19. The method of claim 1, wherein the resin further includes diethyl fumarate (DEF).

* * * * *

UNITED STATES PATENT AND TRADEMARK OFFICE
CERTIFICATE OF CORRECTION

PATENT NO. : 9,688,023 B2
APPLICATION NO. : 13/817612
DATED : June 27, 2017
INVENTOR(S) : H. David Dean et al.

Page 1 of 1

It is certified that error appears in the above-identified patent and that said Letters Patent is hereby corrected as shown below:

On the Title Page

Item "(76)" should read item -- (75) --.

Item (73), Assignee Section, should read -- Case Western Reserve University, Cleveland, OH (US); Envisiontec, Inc., Dearborn, MI (US); University of Maryland, College Park, MD (US); and Rice University, Houston, TX (US) --.

Signed and Sealed this
Twenty-fifth Day of September, 2018

Andrei Iancu
*Director of the United States Patent and Trademark Office*